(12) United States Patent
Meikle et al.

(10) Patent No.: US 8,053,223 B2
(45) Date of Patent: Nov. 8, 2011

(54) **BIOCONTROL OF *VARROA* MITES**

(75) Inventors: William G. Meikle, Clapiers (FR);
Christian Nansen, Lubbock, TX (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 830 days.

(21) Appl. No.: 11/948,340

(22) Filed: Nov. 30, 2007

(65) Prior Publication Data
US 2009/0060880 A1    Mar. 5, 2009

(51) Int. Cl.
*C12N 1/14*    (2006.01)
(52) U.S. Cl. .................................. 435/254.1; 424/93.5
(58) Field of Classification Search ........................ None
See application file for complete search history.

(56) References Cited

U.S. PATENT DOCUMENTS

| 5,516,513 | A  | * | 5/1996 | Wright | 424/93.3 |
| 6,403,085 | B1 | * | 6/2002 | Stimac | 424/93.5 |
| 7,241,612 | B2 | * | 7/2007 | Shapiro-Ilan et al. | 435/254.1 |

OTHER PUBLICATIONS

Crop Protection Monthly, May 31, 2005—Issue 186, pp. 1-18.*

* cited by examiner

*Primary Examiner* — Irene Marx
(74) *Attorney, Agent, or Firm* — John D. Fado; Gail E. Poulos

(57) ABSTRACT

A biopesticide formulation using isolates of the fungus *Beauveria bassiana* has been developed, which can be used to control arachnid infestations of honeybee hives. The formulation is particularly useful for controlling infestations of *Varroa destructor* in honey bee hives.

5 Claims, 12 Drawing Sheets

BIOCONTROL OF *VARROA* MITES

BACKGROUND OF THE INVENTION

1. Field of the Invention

This invention relates to novel formulations for the control of arachnids, especially *Varroa destructor*, an ectoparasite of the honey bee, *Apis mellifera* and to a novel strain of *Beauveria bassiana*. It also relates to methods for treating arachnids, especially *Varroa destructor*, using a formulation having a *Beauveria bassiana* and a carrier.

2. Description of the Related Art

Currently, there are several methods of controlling economically important pests such as *Varroa* mites. These methods fall into two broad categories-chemical and biological. Chemical methods are the most commonly used. However, chemical pesticides can pose risks to human health and cause environmental damage due to adverse effects on non-target insects and other animals. Chemical pesticides can kill pollinating insects, adversely affecting plant life or can upset insect population balances by killing predators or parasitic insects that naturally control the pest population.

Biological methods of controlling economically important pests have become increasingly attractive as a less ecologically destructive way of controlling pests such as arachnids and insects. Biological methods exploit an arachnid's and insect's natural enemies and include using parasitoids, predators and pathogens. Of the various ways to use an arachnid's and insect's natural enemies as biological control agents for that arachnid or insect, one of the most common is mass multiplying pathogens such as bacteria and fungi and applying them to an affected area as a biopesticide. Organisms which have been under investigation as potential biopesticides include viruses, nematodes, protozoa, bacteria, and fungi.

*Varroa* mites (*Varroa destructor* Anderson and Trueman) are an increasingly important pest of honeybees (Chandler et al., Biocontrol Science and Technology, volume 11, pages 429-448, 2001 Rinderer et al., Apidologie, Volume 32, pages 381-394 2001). *Varroa destructor* was found in continental Europe, northern Africa, and South America by 1975 (De Jong et al., Annual Review of Entomology, Volume 27, pages 229-252, 1982) and in the United States in 1987 (Chandler et al., supra). Infested colonies often die within two years. The mites do not cause massive acute mortality, but weaken larvae and adults by feeding on haemolymph, transmitting diseases, and inducing deformities (Chandler et al., 2001, supra; Martin, Journal of Applied Ecology, 2001). The impact of *Varroa* mites on both domesticated and feral colonies of *A. mellifera* in the United States has been profound; feral populations of *A. mellifera*, once common, have been almost completely eliminated by the mites (Rinderer et al, 2001, supra). The loss of wild colonies of *A. mellifera* has been felt most by farmers who depend on the bees for pollination of fruit and field crops.

Chemical control of *Varroa* mites has some drawbacks. Apart from issues of residues in wax and honey, mite populations resistant to the common chemical pesticides, fluvalinate and coumaphos, have been observed (Elzen et al, American Bee Journal, Volume 138, pages 674-676, 1998; Elzen and Westvelt, American Bee Journal, Volume 142, pages 291-292 2002; and Milani, Apidologie, Volume 30, pages 229-234, 1999). Biopesticides, and in particular, entomopathogenic fungi, represent alternatives to chemical insecticides in agricultural systems. Preparations of *Bacillus thuringiensis* are registered for the use against wax moth larvae (*Galleria mellonella* L.) in Europe. Several species of entomopathogenic fungi, including *Beauveria bassiana* (Balsamo) Vuillemin, have been found to infect *Varroa* mites in the laboratory (Kanga et al., Journal of Invertebrate Pathology, Volume 81, pages 175-184, 2002; Shaw et al, Biological Control, Volume 24, pages 266-276, 2002; Davidson et al., Journal of Applied Microbiology, Volume 94, pages 816-825, 2003; Meikle et al., Journal of Apicultural Research, Volume 45, Number 1, pages 39-41, 2006), and both *Hirsutella thompsonii* Fisher and *Metarhizium anisopliae* (Metschinkoff) have been shown to affect mite densities in honey bee colonies (Kanga et al, 2002, supra; Kanga et al., Journal of Economic Entomology, Volume 96, pages 1091-1099, 2003, Kanga et al., Biologist, Volume 52, pages 88-94, 2005).

Several criteria are used in evaluating a fungal biopesticide. The first criterion is the density of the mites in the bee colony, measured either by a) placing a rectangular piece of cardboard covered with glue (hereafter "sticky board") and counting the mites that fall onto the board after a given amount of time; or b) by sampling large numbers of worker bees, treating the bees to remove the mites and then counting the bees and the mites to calculate a mite density per 100 bees. A second criterion is the rate of infection of the target pest, measured by collecting pests, in this case *Varroa* mites, placing them in environmental conditions under which the fungus will sporulate, such as on water agar in petri dishes, and counting the number of individuals that sporulate, compared to number that do not sporulate (the proportion of mite cadavers that sporulate is hereafter referred to as the "proportion infected mites"). The duration of the treatment can be measured as the length of time the infection rate of the pests exceeds background levels, and the spread of the treatment within an area, by movement of treated individuals, such as adult bees, can be measured by recording the infection rate in untreated areas. A third criterion is the impact of the biopesticide on the bee colony itself. Even if a product works well, beekeepers need to know the risk of harming the colony itself. Various forms of *Varroa* mite control are known, however there remains a need in the art for reliable control methods and traps for controlling *Varroa* mites. The present invention, as described below, is different from related art control methods, lures, and traps.

SUMMARY OF THE INVENTION

It is therefore an object of the present invention to provide an entomopathogenic fungus which is virulent to *Varroa* mites without significantly harming non-target insects.

Another object of the present invention is to provide an entomopathogenic fungus which is virulent to *Varroa* mites having the identifying characteristics of *Beauveria bassiana* NRRL 30976.

A further object of the present invention is to provide a biopesticidal composition comprising *Beauveria bassiana* conidia and an acceptable agricultural carrier wherein the conidia are in an effective amount to at least reduce the number of viable *Varroa* mites in honeybee hives.

A still further object of the present invention is to provide a biopesticidal composition comprising *Beauveria bassiana* conidia and a wax powder wherein the conidia are in an effective amount to at least reduce the number of viable *Varroa* mites in honeybee hives.

Another object of the present invention is to provide a biopesticidal composition comprising *Beauveria bassiana* NRRL 30976 and a plant hard wax powder wherein the conidia are in an effective amount to at least reduce the number of viable *Varroa* mites in honeybee hives.

A still further object of the present invention is to provide a method for controlling *Varroa* mites in honeybee hives by applying a biopesticidal composition to the hive wherein said composition comprises *Beauveria bassiana* conidia and an acceptable agricultural carrier wherein the conidia are in an effective amount to at least reduce the number of viable *Varroa* mites in honeybee hives.

A still further object of the present invention is to provide a method for controlling *Varroa* mites in honeybee hives by applying a biopesticidal composition to the hive wherein said composition comprises *Beauveria bassiana* conidia and an acceptable agricultural carrier that is a plant hard wax powder such as carnauba wax powder, candelilla wax powder, and jojoba wax powder; wherein the conidia are in an effective amount to at least reduce the number of viable *Varroa* mites in honeybee hives.

Another object of the present invention is to provide a method for controlling *Varroa* mites in honeybee hives by applying a biopesticidal composition to the hive wherein said composition comprises *Beauveria bassiana* NRRL 30976 conidia and an acceptable agricultural carrier wherein the conidia are in an effective amount to at least reduce the number of viable *Varroa* mites in honeybee hives.

A still further object of the present invention is to provide a method for controlling *Varroa* mites in honeybee hives by applying a biopesticidal composition to the hive wherein said composition comprises *Beauveria bassiana* NRRL 30976 conidia and an acceptable agricultural carrier that is a plant hard wax powder wherein the conidia are in an effective amount to at least reduce the number of viable *Varroa* mites in honeybee hives.

Further objects and advantages of the invention will become apparent from the following description.

Deposit of the Microorganisms

*Beauveria bassiana* (Balsamo) Vuillemin (Deuteromycota: Hyphomycetes) isolate Bb05002 NRRL 30976 has been deposited on Oct. 5, 2006 under the provisions of the Budapest Treaty, with U.S.D.A. Agricultural Research Service Patent Culture Collection (National Center for Agricultural Utilization Research, 1815 N. University Street, Peoria, Ill. 61604).

BRIEF DESCRIPTION OF THE DRAWINGS

FIG. 1A is a graph showing the estimated weights of adult bee over time for an experiment using 4 beehives treated with either wax powder+conidia (black columns) or wax powder alone (gray columns). Vertical dashed line shows day of treatment.

FIG. 1B is a graph showing the average surface area of sealed brood, in square centimeters (measured on the beehive frames), for an experiment using 4 beehives treated with either ENTOSTAT® powder+conidia (black columns) or ENTOSTAT® powder alone (gray columns). Vertical dashed line shows day of treatment.

FIG. 2 is a graph showing the average daily mite fall per hive for bee hives treated with *B. bassiana* conidia and ENTOSTAT® powder (solid line), ENTOSTAT® powder only (dashed line), or nothing (control; dotted line). Points with an asterisk indicate a significant difference between hives treated with conidia and control hives (probability of error is 0.05) on that day. Vertical dashed line shows day of treatment.

FIG. 3A is a graph showing the average proportion infected mites over time for hives treated with *B. bassiana* conidia and ENTOSTAT® powder (solid line), ENTOSTAT® powder only (dashed line), or nothing (control; dotted line). Vertical dashed line shows day of treatment.

FIG. 3B is a graph showing the average daily mite fall per hive over time for hives treated with *B. bassiana* conidia and ENTOSTAT® powder (solid line), wax powder only (dashed line), or nothing (control; dotted line). Vertical dashed line shows day of treatment.

FIG. 3C is a graph showing the average proportion infected mites for hives treated with *B. bassiana* conidia and ENTOSTAT® powder (solid line), ENTOSTAT® powder only (dashed line), or nothing (control; dotted line). Vertical dashed line shows day of treatment.

FIG. 3D is a graph showing the average daily mite fall per hive over time for hives treated with *B. bassiana* conidia and ENTOSTAT® powder (solid line), ENTOSTAT® powder only (dashed line), or nothing (control; dotted line). Vertical dashed line shows day of treatment.

FIG. 4 is a graph showing the average number of *B. bassiana* colony-forming units ("cfu"—the number of colonies counted on a petri dish containing agar and coated with a dilute detergent solution that was used to wash the bees) per adult bee by treatment over time. Bars show back-transformed standard error intervals. Within each sampling occasion, points with an "a" on top indicate that the treated colonies were significantly different (Tukey's HSD with probability of error of 0.05) from both the powder only and control treatment, and with a "b" on top indicate the treated colonies were significantly different only from the control colonies. Vertical dashed line shows day of treatment.

FIG. 5 is a graph showing the proportion of infected mites in response to *B. bassiana* cfu (see description of FIG. 4 above) density per bee. Each observation is from a single hive showing cfu density from one sampling date and daily mite samples averaged around that date; no mite samples appears twice. Eighteen observations with zero cfu density are not shown. They had an average proportion infected mites of 0.16±0.13 standard deviations. Filled circles: conidia+ENTOSTAT® powder treatment; empty circles: ENTOSTAT® powder alone treatment; triangles: control.

FIG. 6 is a graph showing the average intrinsic rates of increase of bee colonies treated with *B. bassiana* conidia plus ENTOSTAT® wax powder, conidia plus wheat flour, flour alone, or nothing (control), and showing the ambient temperature. Vertical dashed line shows day of treatment.

FIG. 7A is a graph showing the average proportion fallen mites that were infected per colony over time for bee colonies treated with either *B. bassiana* conidia plus ENTOSTAT® wax powder, conidia plus wheat flour, flour alone, or nothing (control). Vertical dashed line shows day of treatment.

FIG. 7B is a graph showing average (geometric) daily mite fall on to sticky boards for bee colonies treated with either *B. bassiana* conidia plus ENTOSTAT® wax powder, conidia plus wheat flour, flour alone, or nothing (control). Vertical dashed line shows day of treatment.

FIG. 8 is a graph showing the average proportion fallen mites that were infected per colony over time for bee colonies treated with either *B. bassiana* isolate 05002 conidia plus carnauba wax powder (applied twice), *B. bassiana* isolate GHA conidia plus carnauba wax powder (applied twice), *B. bassiana* isolate 05002 conidia plus candelilla wax powder (applied once), candelilla wax powder alone (applied twice), or nothing (control). Vertical dashed line shows day of treatment.

FIG. 9 is a graph showing the average (geometric) daily mite fall on to sticky boards over time for bee colonies treated with either *B. bassiana* isolate 05002 conidia plus carnauba wax powder (applied twice), *B. bassiana* isolate GHA conidia plus carnauba wax powder (applied twice), *B. bassiana* isolate 05002 conidia plus candelilla wax powder (applied once), candelilla wax powder alone (applied twice), or nothing (control). Vertical dashed line shows day of treatment.

FIG. 10 is a graph showing the average number of *B. bassiana* "cfu" (see above) per adult bee by treatment over time. Bees were collected from colonies treated with either *B. bassiana* isolate 05002 conidia plus carnauba wax powder (applied twice), *B. bassiana* isolate GHA conidia plus carnauba wax powder (applied twice), *B. bassiana* isolate 05002 conidia plus candelilla wax powder (applied once), candelilla wax powder alone (applied twice), or nothing (control). Vertical dashed line shows day of treatment.

DETAILED DESCRIPTION OF THE INVENTION

Figure 1:
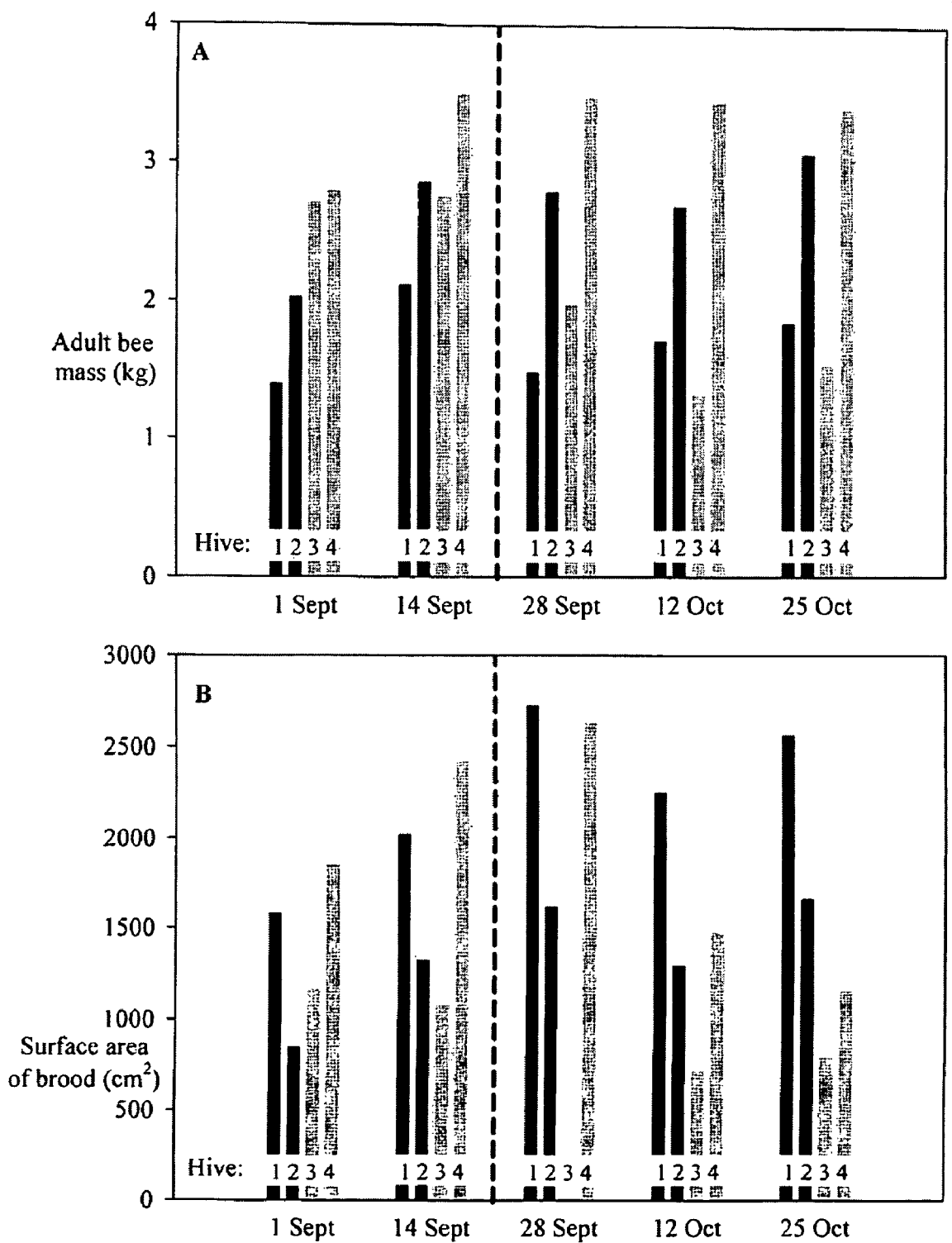

*Varroa* mites are honey bee ectoparasites. They have devastated the honey bee industry in North America and Europe. Pesticides are the usual alternative for beekeepers with infested hives, but in addition to potentially contaminating honey and wax, these pesticides are rapidly losing effectiveness because pesticide-resistant mites have become more and more common. Entomopathogenic fungi have been proposed as biological control agents against *Varroa* mites. In collections of mites from over 100 bee colonies, *B. bassiana* was the only entomopathogenic fungus identified and one isolate from this collection was selected for field testing as a component of a biopesticidal composition comprising a fugal conidia a powder. The entomopathogenic fungus *Beauoveria bassiana* is an imperfect fungus (Fungi Imperfecti) and the subdivision Deuteromycotina. The genus *Beauveria* Vuill. is within the Class Deuteromycetes and is distinguished from other genera by having conidia that are borne singly, not catenulate and having the fertile portion of the conidiophore zig-zag in shape and drawn out at the tip. The species *Beauveria bassiana* has spherical, not ellipsoid, conidia measuring 2-3 micrometers by 2-2.5 micrometers and with conidiophores forming dense bunches. *Beauveria bassiana* is the first known entomopathogenic fungus naturally occurring in beehives which is effective as a biopesticide against *Varroa* mites in infested honeybee hives.

Like most entomopathogenic fungi, *Beauveria bassiana* initiates infection by a germinating spore (conidium) attaching to and subsequently penetrating the cuticle of the arachnid or insect host. *Beauveria bassiana* attaches very securely to the cuticle of the targeted arachnid or insect pest. As the fungus penetrates the target pest cuticle, the invasive hyphae begin to enter the host tissues and ramify through the hemocoel. Hyphal bodies or segments of the hyphae distribute throughout the hemocoel, filling the dying arachnid or insect with mycelium. Emergence hyphae grow out through the insect's integument and produce spores on the external surface of the host. These spores, or conidia, are dispersed and capable of infecting new host arachnid or insect pests.

The term entomopathogenic fungus means a fungus capable of killing an arachnid or an insect. Such a fungus is considered a mycopesticide. Entomopathogenic fungi include those strains or isolates of fungal species in the class of Hyphomycetes which possess characteristics allowing them to be virulent against arachnids and insects. These characteristics include formation of stable infective conidia. An effective entomopathogenic fungus preferably is lethal for target arachnid and insects but less harmful for non-target insects.

The term strain of "*Beauveria bassiana*" is intended to include strains of *B. bassiana* (Balsamo) Vuillemin (Deuteromycota: Hyphomycetes) or isolates of *B. bassiana* that are virulent against *Varroa* mites. Strains of *B. bassiana* typically produce high concentrations of stable conidia that are infective by insect and arachnid cuticle penetration, producing infection with morbidity in two to four days and insect and arachnid death at three to ten days. An example of an isolate of *Beauveria bassiana* is isolate Bb05002 NRRL 30976 which is a virulent strain of fungus with respect to *Varroa* mites. *B. bassiana* has limited effects on honeybees hives or colonies.

The phrase "without significantly harming non-target insects" means that insects are not infected and killed by the entomopathogenic fungus at dose rates which kill arachnids such as *Varroa* mites. It is important that non-target insects are not significantly harmed by the entomopathogenic fungus under conditions which the fungus is effective in the field as a mycoinsecticide for arachnids such as *Varroa* mites.

The term $LT_{50}$ means the time needed for the entomopathogenic fungus to kill half the arachnids or insects at a given dose and under given ambient conditions. For the present invention, the $LT_{50}$ of a fungus is measured in number of days until half of the treated *Varroa* mites are dead. An aqueous suspension with a known concentration of fungal conidia is made, a known amount of the suspension is applied to *Varroa* mites using a spray tower, and the treated mites are then kept alive on bee pupae. At the same time, untreated mites are kept on different bee pupae (the "control") to ensure that the experimental conditions are otherwise healthy for the mites. The bee pupae are kept under controlled temperature and humidity and monitored daily for mortality of mites. The data acquired is then analyzed by known methods to determine the $LT_{50}$ of the entomopathogenic fungi with respect to *Varroa* mites. The $LT_{50}$ of the present invention is approximately 5 to 8 days at a dose concentration of $10^7$ conidia per ml and with the mites subsequently kept at 30 degrees C. and 70% relative humidity.

The term "conidia" is art-recognized and intended to include asexual spores characteristic of many fungi including the presently described entomopathogenic fungus. Conidia of a fungus can be counted and used as units of measure of the fungus, for example, with respect to viability and $LT_{50}$.

The present invention also pertains to formulations containing conidia of the presently described entomopathogenic fungus. Formulations include conidia of the fungus of the present invention in combination with a carrier. The carrier includes a powder, preferably a plant hard wax powder and hydrated silica. The ratio of hydrated silica to wax powder is approximately 1 part silica to 200 parts wax powder (weight/weight). Examples of powders useful in the present invention include carnauba wax powder, candelilla wax powder, jojoba wax powder, etc. This biopesticide composition comprises the entomopathogenic fungus having virulence against the targeted arachnid pests and a plant hard wax powder. The term "powder" means a composition that consists of finely dispersed solid particles that are free flowing and capable of being readily dispersed. The powder can be any plant hard wax powder which enables it to mix with fungal spores and the arachnid cuticle.

The language "entomopathogenic formulation" is intended to include a mixture of conidia of an entomopathogenic fungus such as *Beauvaria bassiana*, and particularly strain Bb05002 and a carrier. The carrier is a substance capable of dispensing conidia of the fungus appropriately without affecting the fungus' ability to perform its intended function. Carriers are as described above.

The present invention provides methods of killing *Varroa* mites using the aforementioned formulations. The formulation is applied to affected hives by blowing the formulation into the hives using any means for applying a dust to bee hives such as a powder dusting device as is known in the art.

Infection rates of *Varroa* mites in field experiments exceeded 60% for at least two weeks after treatment. Untreated hives also experienced peaks in the infection rate, although significantly lower than in the treated hives, which indicates movement of bees from treated hives to untreated hives.

*Beauveria bassiana* may be cultured and mass produced by methods used to culture *Beauveria* spp. See for example, U.S. Pat. No. 4,925,663; Microbial Control of Pests and Plant Diseases 1970-1980, published by Academic Press, pages 471-473 (1981; edited by H. D. Burges); and Feng et al., J. Invertebrate Pathology, Vol. 46, no. 3, November 1985, page 260, the disclosures of which are hereby incorporated by reference.

*Beauveria bassiana* does not harm honeybee colonies. The entomopathogenic fungus is non-toxic to consumers and/or users and also does not detrimentally affect the worker bees, honey combs and honey produced by the honeybees. These characteristics make it particularly well suited to the control of *Varroa* mites in honey bee hives and include:

Virulence toward *Varroa* mites;
Efficient production of stable, infective conidia,
Limited pathogenicity or infectivity to honeybees colonies, and
No adverse effects on vertebrates.

The entomopathogenic fungus of the present invention which is effective against *Varroa* mites, can be stored and transported in commercial distribution channels without special handling and has fewer adverse effects on non-target species, including humans and the environment than chemical pesticides.

As noted above, in the discussion of the *Beauveria bassiana*, the mode of infection of fungi is generally by cuticular penetration by the germ tube of the fungal conidia and may also occur through the respiratory or alimentary tract (such as mouth parts). Additionally, ingestive fungal spores voided in the feces may provide another source of contact with the cuticle of the targeted arachnid pest. Death in the host may occur either by release of fungal toxins or by tissue destruction. The fungal growth range is between about 15 degrees C. and about 34 degrees C. in a wide range of relative humidity with high humidity necessary for spore germination on target organisms.

The following examples are intended only to further illustrate the invention and are not intended to limit the scope of the invention as defined by the claims. One of ordinary skill in the art will be able to substitute another plant hard wax given the detailed description of the present invention. *Beauvaria bassiana* NRRL 30976 is used as a model for the present invention. Any *B. bassiana* having the above described characteristics is useful in the present invention.

EXAMPLE 1

Apiaries were visited at several locations. At each apiary, a metal tray was placed under each hive, the hives were opened and approximately 150 grams of powdered sugar was poured into the brood box, making an effort to divide it among all the between-frame spaces. Powdered sugar has been shown to be effective in knocking down *V. destructor* on adult honey bees (Fakhimzadeh, Apidologie, Volume 32, pages 139-148, 2001). The hives were then closed and about 20 minutes later all the material that had collected on the tray was poured into a sealed plastic box. The boxes were transported to the laboratory and all *Varroa* mites were placed on water agar (about 6 grams/liter) with chloramphenicol (about 0.4 grams/liter) to reduce bacterial growth, incubated for about two weeks at about 23° C. and observed for at least three weeks for sporulation. Any entomopathogenic fungi collected were used to inoculate two types of media: Sabouraud dextrose agar with yeast (SDAY) (Goettel and Inglis, 1997, supra) and semi-synthetic INRA media (Meikle et al. Journal of applied Entomology, Volume 129, pages 315-322, 2005), both with chloramphenicol (about 0.4 grams/liter), in plastic petri dishes (about 3.5 cm diameter). The most vigorous cultures were purified through a series of two to three isolations on average, and grown as pure cultures.

A total of 8 *B. bassiana* isolates were recovered from the exploration. Two of these were selected for bioassay evaluation.

EXAMPLE 2

Isolates from Example 1 were evaluated, as well as several *Metarhizium anisopliae* (Metschnikoff) Sorokin (Deuteromycota: Hyphomycetes) isolates from the collection of entomopathogenic fungi at the European Biological Control Laboratory (EBCL) in bioassays using *Varroa* mites kept on bee pupae. Cultures of candidate fungal isolates were grown on SDAY with chloramphenicol and harvested after about 12-14 days. For each experiment, the viability of the conidia was assessed by plating a sample of the suspension onto SDAY, incubating the plates at about 23° C. for about 24 hours, and examining about 200 conidia for germ tubes under a light microscope. Prior to the bioassay, bee pupae were collected from hives by cutting sections of brood comb from the frame, placing the pieces in a sterile plastic box and, in the lab, carefully extracting the pupae and placing them individually in small (about 2×2×1 cm) plastic boxers with screen covers. Any *Varroa* mites found on the pupae upon their removal from the comb were destroyed. A suspension containing about $10^7$ conidia/ml was prepared by suspending a quantity of conidia in about 10 ml of about a 0.1% aqueous solution of TWEEN 80 poured into 50 ml bottles filled with glass beads and agitated for about two minutes using a Vortex Genie 2 (Scientific Industries, Bohemia, N.Y., USA). Thirty *Varroa* mites were placed in a petri dish (about 9 cm diameter) lined with moist filter paper, placed in a spray tower (Burkard Manufacturing Ltd., Herts., England) and sprayed with either an aqueous TWEEN 80 solution (no conidia) or the conidial suspension. The spray tower had an air pressure of about 0.74 $kg/cm^2$ and delivered an average of about 714 conidia/mm using suspensions of about $5\times10^7$ conidia/ml (Meikle et al., 2005, supra). After exposure, *Varroa* mites were placed on the bee pupae at the density of two mites per pupa. All the small boxes containing the mites and bee pupae were placed in a large plastic box kept at about 85% relative humidity using a saturated KCl solution, and the box was placed in an incubator at approximately 30 degrees C. Each cell was inspected about every 2-3 days until all mites in both treatments were dead, and bee pupae were replaced twice a week. Dead mites were immediately placed on water agar containing chloramphenicol, kept at about 23 degrees C. and examined after two weeks for signs of sporulation.

Of the 8 total isolates examined in the bioassay, 7 were found to significantly lower mite survivorship relative to the control. Median survivorship of mite treated with B05002 was about 5 days in the first bioassay and 8 days in the second (See Table 1 below) and this isolate was selected for use in the field experiments.

TABLE 1

Bioassay results.

| ISOLATE | ORIGIN | MEDIAN SURVIVORSHIP (DAYS) | WILCOXON CHI SQUARE | PROBABILITY |
|---|---|---|---|---|
| Bb05002 ($1^{st}$) | Varroa mite | 5 | 26.96 | <0.0001 |
| Bb05002 ($2^{nd}$) | Varroa mite | 8 | 20.62 | <0.0001 |
| Bb05005 | Varroa mite | 6 | 13.745 | 0.0002 |
| Meta 03015 | Termite | 3.5 | 23.54 | <0.0001 |
| Meta 03019 | Termite | 3.5 | 22.63 | <0.0001 |
| Meta 92204 | Soil | 5 | 26.51 | <0.0001 |
| Meta 92206 | Soil | 3 | 3.90 | 0.048 |
| Meta 92209 | Soil | 13 | 0.36 | 0.548 |

The Wilcoxon Chi square statistic was used to compare survivorship of mites treated with conidia to control mites. The median survivorship of mites in the control group ranged from about 15.5 days to about 26 days (from Meikle et al., 2006, supra).

EXAMPLE 3

Eight bee colonies, four established one year and one month before the other, were maintained in painted, 10-frame wooden Dadant brood boxed (561 capacity) (Ickowicz, Bollene, France). The hives were covered with telescoping lids with a weight placed on top to stabilize the hive in wind. The hives were arranged in two groups of four hives each, about 4 meters apart. Within each group, hives were kept about 50 cm apart. Permanent water sources existed less than about 1 km away. In order to monitor changes in hive weight during the course of the experiment, four of the hives, two in each hive group, were placed on top of two short wooden planks resting on stainless steel electronic balances (TEKFA® model B-2418, Galten, Denmark). The balances had about a 100 kg maximum capacity, a precision of about 10 grams, and an operating temperature range of about −30 degrees C. to about 70 degrees C. The balances were linked to 12-bit dataloggers (Hobo® U-12 External Channel datalogger, Bourne Mass., USA) and powered by a solar panel (BP Solar model 1230, Mimeure, France). The weighing system had an overall precision of about 30 g. The adult bee mass for the hives kept on the scales was estimated every two weeks, starting about three weeks before treatment, by weighing each brood box frame and the super separately with a portable electronic balance (Kern and Sohn model 12K 1N, Balingen, Germany), after shaking them free of bees, and subtracting the combined weight of the frames containing brood, honey, and pollen and non-colony components from the total hive weight.

Cultures of *Beauveria bassiana* (Balsamo) Vuillemin (Deuteromycota:Hyphomycetes( ) isolates Bb05002, NRRL 30976 isolated from *Varroa* mites, were grown on Sabouraud dextrose with yeast (SDAY) as in Example 1 for about 15 days. Conidia were harvested by scraping the tops of the cultures onto glass Petri dishes with a metal spatula, and the Petri dishes placed in a crystallizing dish containing silica gel for drying. The viability of the conidia was assessed by plating a suspension sample onto SDAY, incubating the plates at about 23 degrees C. for about 24 hours and examining about 200 conidia for germ tubes under a light microscope.

Conidia were formulated as follows: Approximately 0.77 grams of conidia of the Bb05002 strain were mixed with about 20.0 grams of ENTOSTAT® powder, a highly refined and electrostatic-charged carnauba wax (Exosect, Southampton, UK) and about 0.10 grams hydrated silica (Hi-Sil-233, Pittsburgh Plate Glass, Pittsburgh, Pa., USA) using a food processor (Valentin Mini Chopper, SEB, Dijon, France). The density of viable conidia per gram formulation was determined by plating onto potato-dextrose agar (PDA) three 0.1 ml sub-samples of the formulation diluted in distilled water to a concentration of approximately 1000 spores/ml, and counting the number of colonies about ninety-six hours after plating. *Varroa* sticky boards (Mann Lake Ltd., Hackensack, Minn., USA) were placed under eight hives in an apiary. About six days later, the sticky boards were collected from beneath each hive and replaced. Two hives on balances were selected for treatment, one hive approximately 2 years old and the other approximately six months old. For each treated hive, a plastic laboratory squirt bottle was filled with about 10.0 grams of the Bb05002 conidia formulation and the formulation was blown between all the frames in the brood box. As a blank control, the other two hives on balances were treated in a similar fashion using about 10.0 grams ENTOSTAT® powder and about 0.05 grams silica per hive. The density of conidia in this experiment was approximately $7.95 \times 10^9$ conidia per gram of formulation. Conidia viability was approximately 91%. The remaining hives in the apiary were not treated.

Sticky boards were removed and replaced approximately every two days after treatment, to reduce contamination due to formulation on the boards. For the following about 15 days, each hive had two sets of boards, with a given board being used on alternate days. All the mites falling on each board were counted daily, removed from the board, and those mites plated on water agar with chloramphenicol. After 15 days, sticky boards were replaced twice a week, all mites counted, and 40-mite samples were plated. After plating, all mite samples were incubated at about 23 degrees C. and examined for sporulation after about 15 days. The day before treatment, and at about 1, 3, 8, 16, and 24 days after treatment, samples of approximately 20 bees per hive were collected in small plastic bags and immediately placed in a freezer. About three weeks later, three 5 bee subsamples from each hive were removed from the bags and vortexed separately of about 3 minutes in approximately 50 ml of about a 0.1% aqueous solution of TWEEN 80. Aliquots of about 20 μl and 100 μl of the resulting suspension of each subsample were spread onto each of three Petri dishes containing SDAY with chloramphenicol, thus 9 plates for each sampling session. The dishes were incubated for about 10 days at about 23 degrees C. and the number of *B. bassiana* colonies were counted in the plates with about 20 μl; when conidia densities became low, the colonies were counted on the 100 μl plates.

Mites were not surface sterilized prior to plating for two reasons: many mites, when removed from the sticky boards, were damaged, and the sterilization procedure may have killed an incipient infection; and because sticky boards were replaced within 2 to 3 days after treatment, thus removing from the system the formulation that fell through the hive during that period, it was seen as unlikely that the boards would be a major source of contamination of the mites.

Data were analyzed using SAS and JMP (SAS Institute, Inc., Cary N.C., USA) software. Multiple regression analyses ($\alpha=0.05$) were analyzed with a linear mixed model using PROC MIXED of SAS (Littell et al., SAS Institute, Cary, N.C., USA, 1996) with either daily mite fall (square root-transformed), proportion infected mites (arcsine-square root-transformed) or cfu density per bee (log $\{x+1\}$-transformed) as response variable and with 3 fixed effects: treatment, date and their interaction. Hive number was incorporated in the analysis as a random effect. The degrees of freedom were calculated using the Satterthwaite method. For each variable, the covariance matrix of the response variable was inspected for patterns and residual plots were assessed visually to check variance homogeneity. Insignificant main effects were excluded from the model but if the interaction was significant both main factors were retained. Because excess formulation on sticky boards immediately after treatment may cause spurious infection data, the first sample after treatment was excluded from each of the analysis of proportion infected mites. Conidia density was $7.95 \times 10^9$ conidia per g formulation.

Adult bee masses were never significantly different between the powder only treatment and the conidia+powder treatment (t test within sampling occasion, $\alpha=0.05$) (FIG. 1). One hive treated with powder only lost its queen in the first half of September; although the queen was replaced before the start of the experiment, a visual inspection of the frame photos for that one hive (hive 3) showed an absence of brood at the first sampling after treatment. Because of the importance of brood to *Varroa* dynamics, mite fall data for hive 3 were excluded from statistical analyses, although data on percentage infected mites for hive 3 were retained. Only one other hive (hive 4) was treated with powder alone, so the powder treatment was removed from the mite fall analyses.

Figure 2:
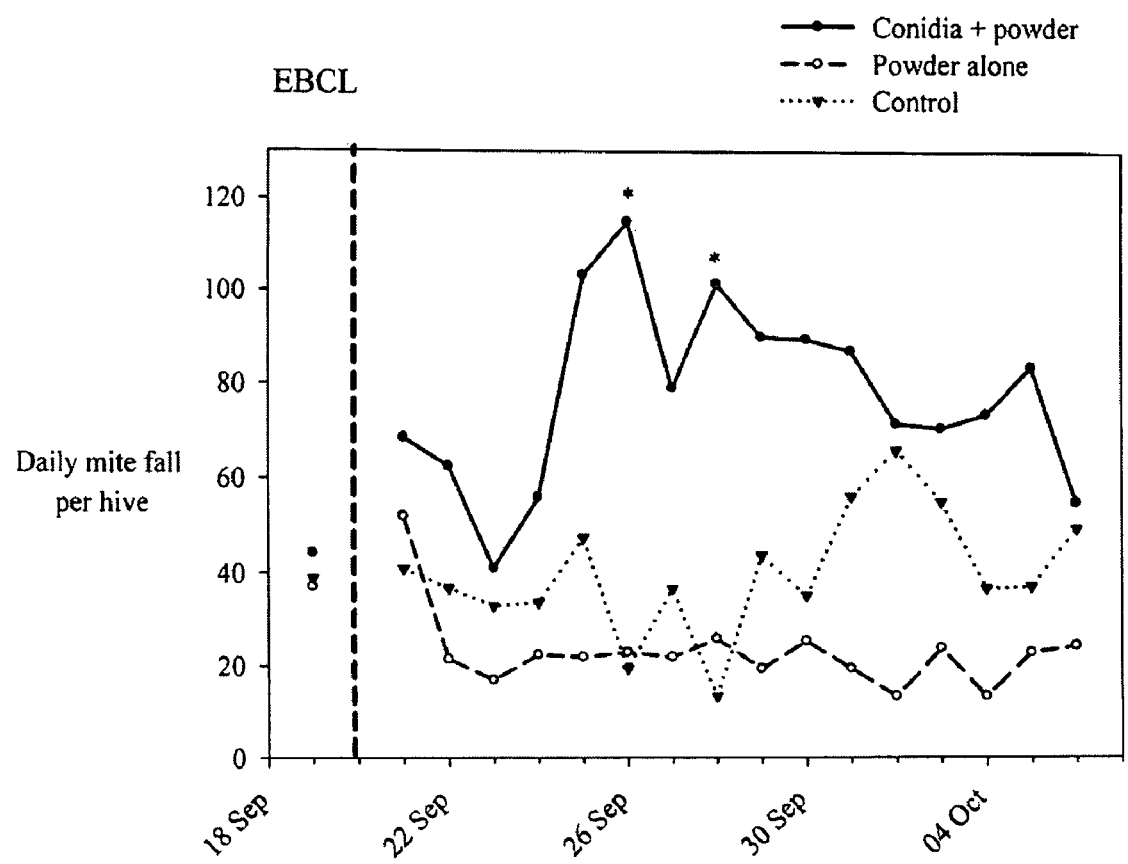

The average daily mite fall per hive was calculated for the first 17 days after treatment (FIG. 2). Mixed-model analysis of mite fall showed that while treatment was not significant ($F_{1,4}=1.60$, $p=0.274$), both date ($F_{13,52}=2.45$, $p=0.0113$) and their interaction ($F_{13,52}=4.38$, $p<0.0001$) were, indicating that mite fall did exhibit significant change over time and that the relationship between the treated and control hives varied over time. Post hoc contrasts showed that hives treated with conidia had significantly higher mite fall than control hives on 26 ($F_{1,5}=8.13$, $p=0.0333$) and 6 and 8 days after treatment ($F_{1,5}=7.33$, $p=0.0398$), which was when maximum treatment effect was expected based on laboratory bioassays. Treatment caused widespread infection of mites in the treated hives in both experiments, with some infection in untreated hives as well due to movement of bees from treated hives to untreated hives, and the effect lasted over a month after treatment.

Figure 3:
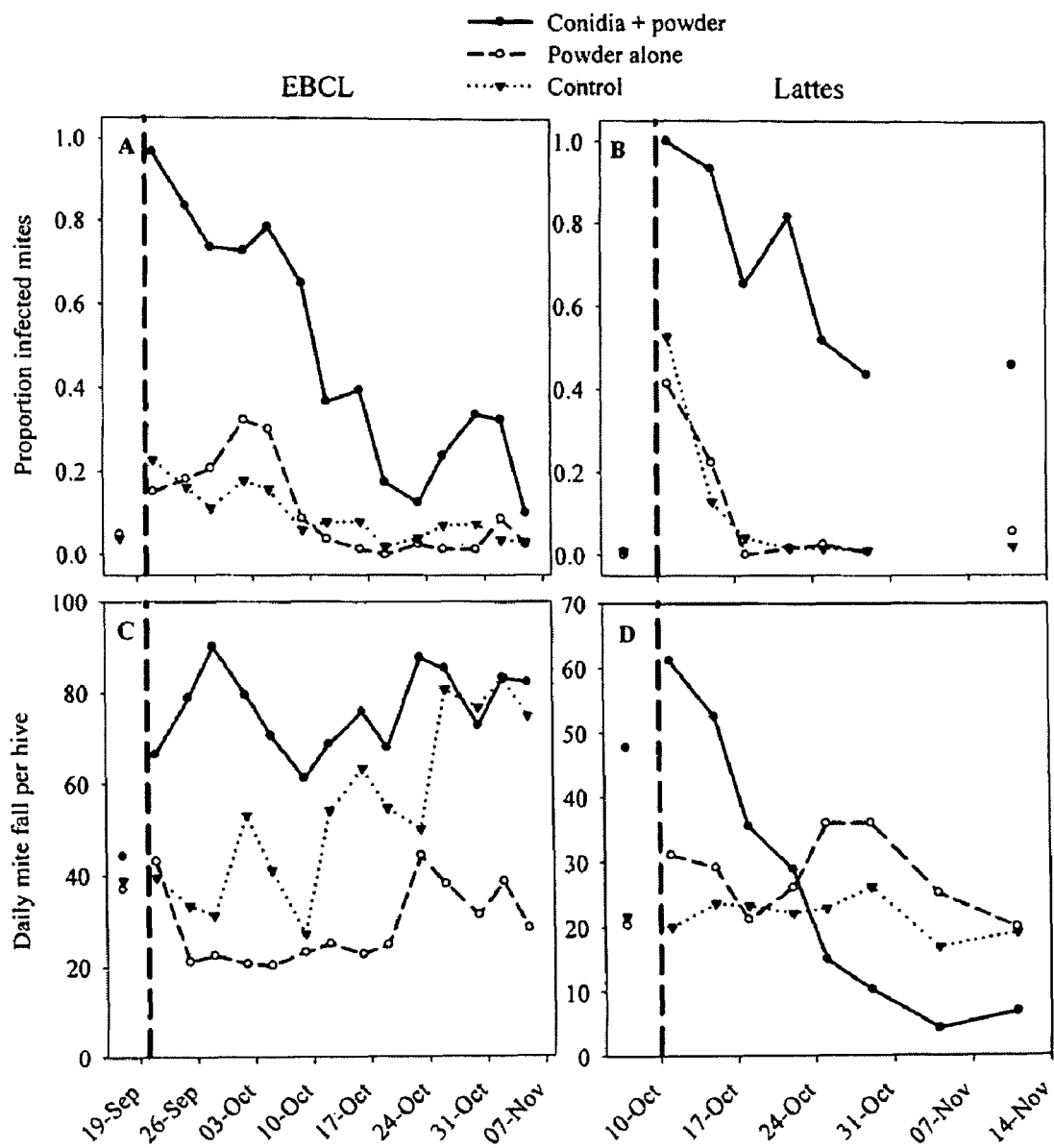

The daily data up to 17 days after treatment were pooled to generate semi-weekly data and combined with later data collected twice per week (FIG. 3). A mixed-model analysis of this semi-weekly data was conducted for both percentage infection and for mite fall. In the percentage infection analysis, both treatment and date were significant ($F_{2,5}=60.78$, $p=0.0003$ for treatment and $F_{12,60}=11.96$, $p<0.0001$ for date) but interaction was not ($F_{24,60}=3.16$, $p=0.089$), indicating that treatment caused a significant increase in the incidence of infection and that the percentages varied over time. The non-significant interaction means that the treatment effects on the transformed scale were approximately constant. After removing the interaction term and re-analyzing the data using treatment contrasts with the Bonferroni adjustment, the conidia+powder treatment was shown significantly different from both the powder only treatment ($t_7=6.06$, $p=0.0015$) and from the control ($t_7=6.61$, $p=0.0009$). After treatment, infected mites were found in substantial numbers also in untreated hives in both experiments. In the mite fall analysis, none of the factors was significant ($F_{1,4}=0.22$, $p=0.665$ for treatment; $F_{12,48}=1.95$, $p=0.052$ for date; $F_{12,48}=1.02$, $p=0.444$ for interaction). After removing the interaction term and re-analyzing the data, date was significant ($F_{12,60}=2.65$, $p=0.0065$) but treatment was not ($F_{1,4}=0.22$, $p=0.665$).

Figure 4:
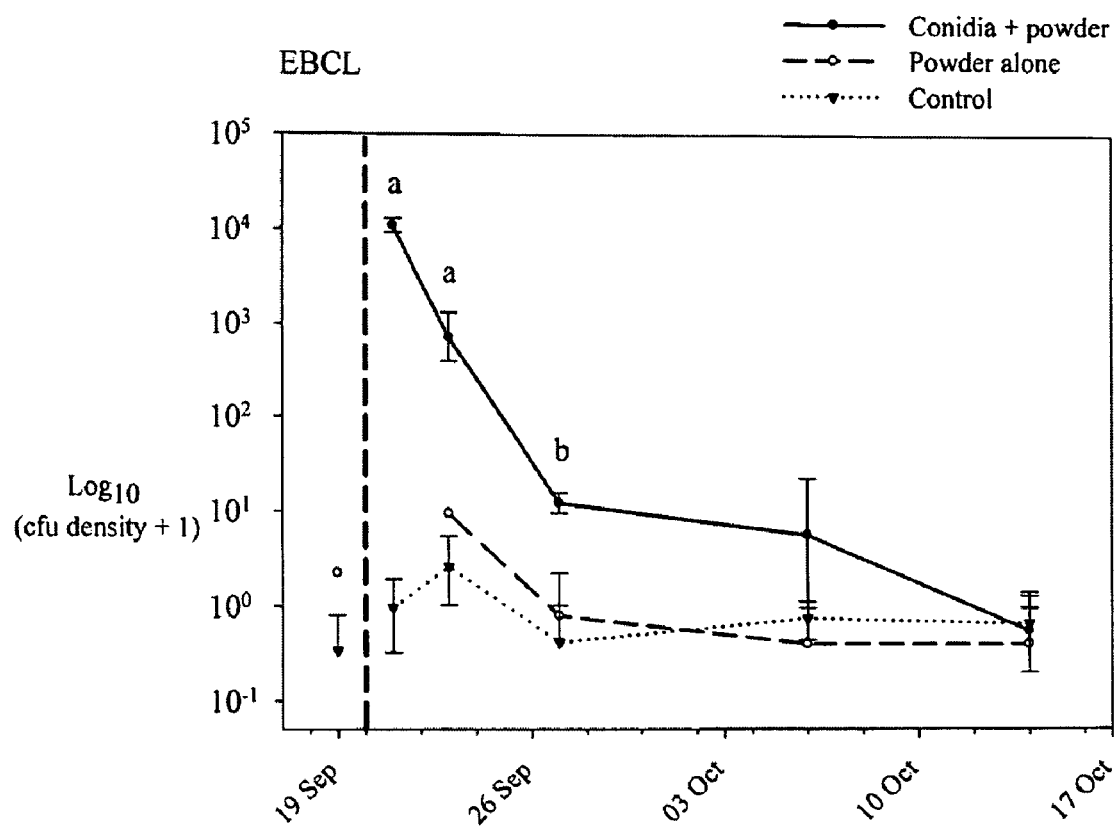
Figure 5:
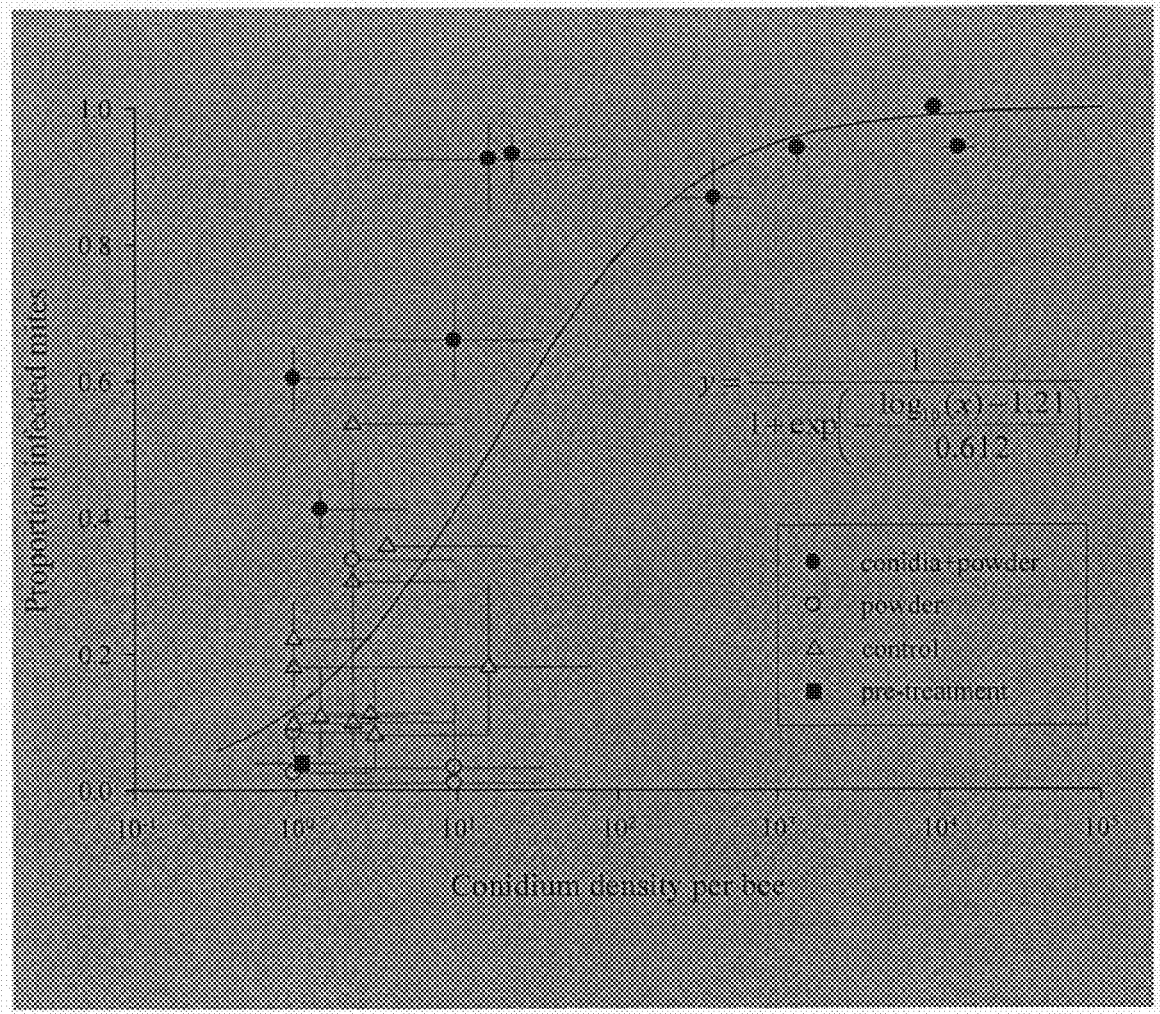
Figure 6:
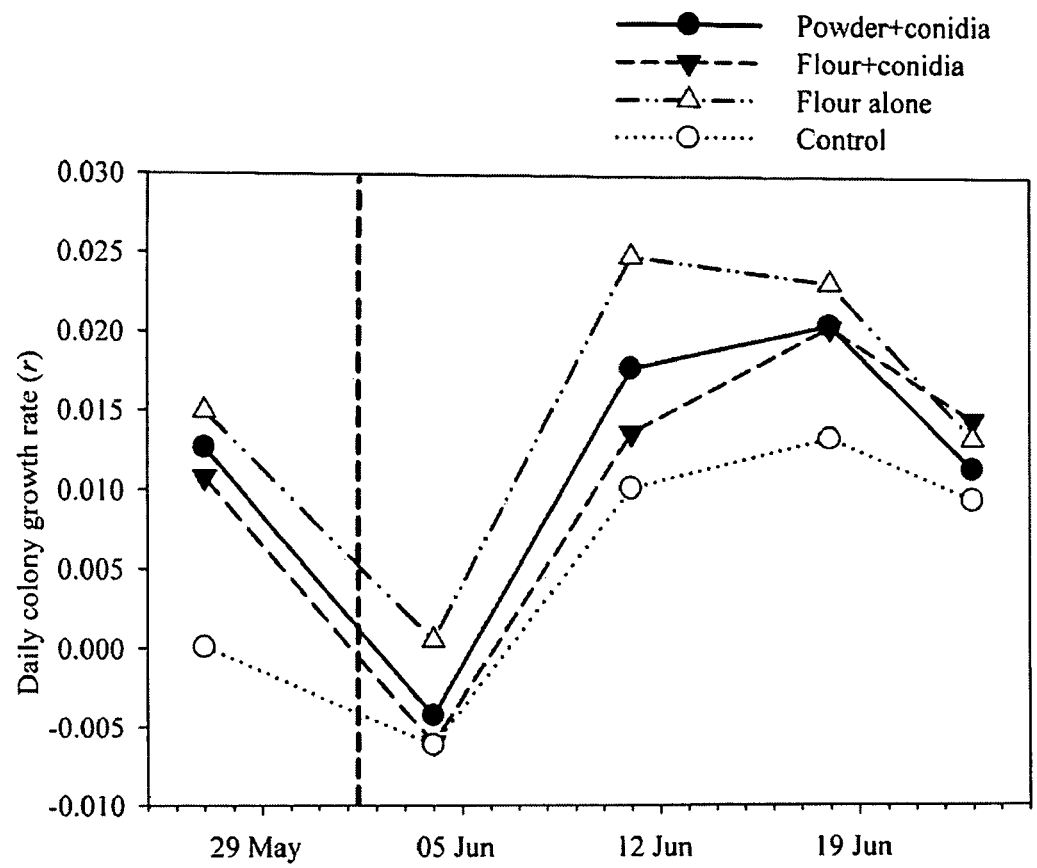
Figure 7:
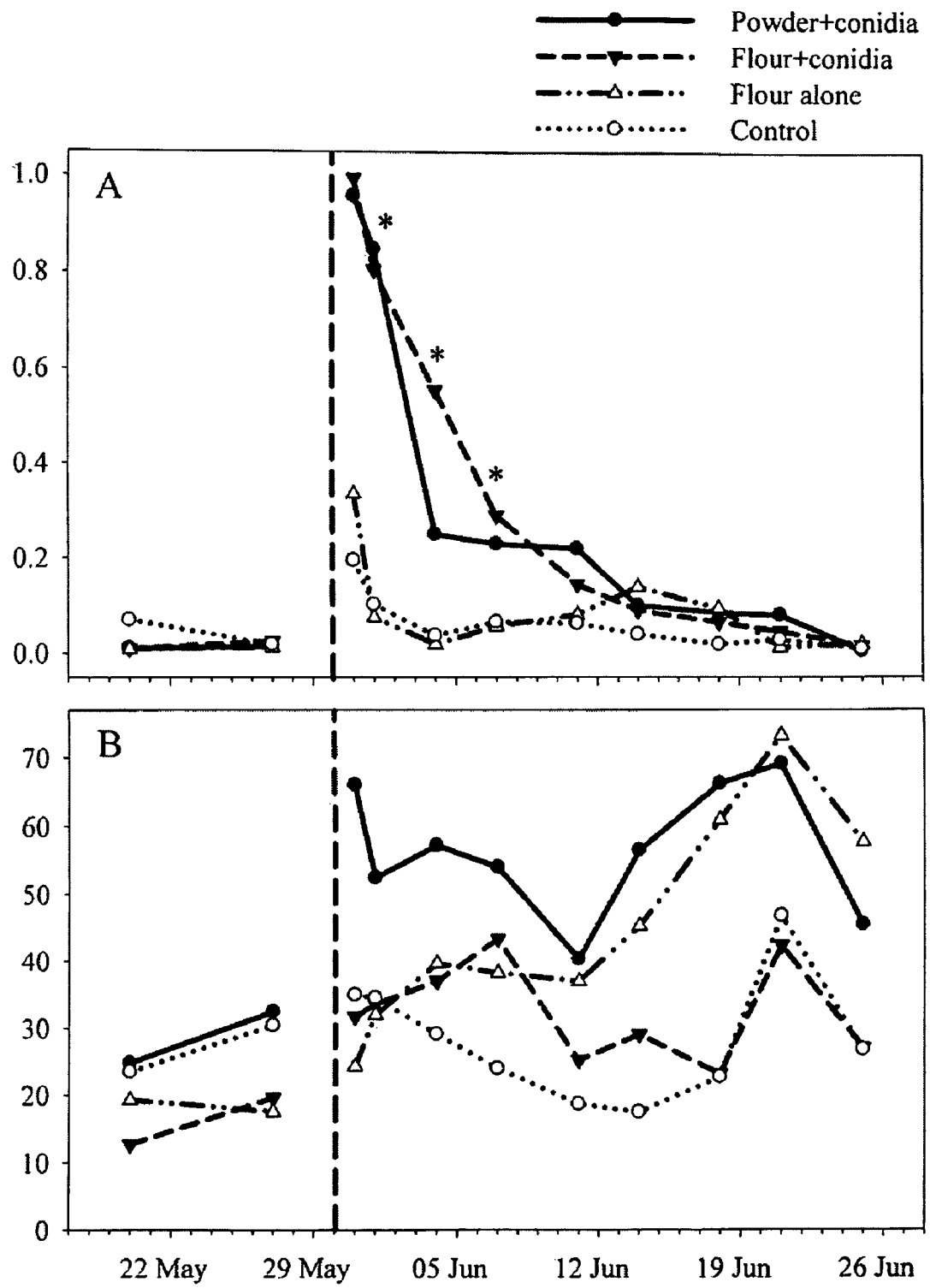

Analysis of the cfu density per bee showed that treatment ($F_{2,5}=43.68$, $p=0.0007$), date ($F_{4,20}=30.40$, $p<0.0001$) and their interaction ($F_{8,20}=20.24$, $p<0.0001$) were significant. Low numbers of *B. bassiana* cfu, averaging about 1 cfu per bee, were found the day before treatment (FIG. 4). The day after treatment the number of cfu peaked at an average of about $1.1 \times 10^4$ cfu per bee in the treated hives, and declined rapidly thereafter. Elevated cfu levels were also observed in bees from control hives and those treated only with powder. However, the average levels never exceeded 10 cfu per bee in the powder-only treatment and 3 cfu per bee in the control. After 24 days, cfu densities on bees were very similar among treatments, and were similar to the pre-treatment level. The response of percentage infected mites to cfu density on bees was sigmoid (FIG. 5).

EXAMPLE 4

In another experiment, similar to Example 3, ten hives were identified in an apiary containing 60 hives. Balances were not used. Experimental hives were separated by one or more hives not included in the experiment. Sticky boards were placed under all hives one week prior to treatment and replaced just after treatment. Four hives were each treated, using the technique describe above in Example 3, with the formulation containing about 1.0 gram of strain Bb05002 conidia plus approximately 10 grams of ENTOSTAT® powder plus approximately 0.05 grams hydrated silica (HiSil). The density of conidia per gram of formulation was about $1.26 \times 10^{10}$. Conidia viability was approximately 91%. Three hives were treated with the powder only, and four hives were included as controls. Boards were replaced about every 3-4 days after treatment for about three weeks and weekly thereafter for about two weeks. All mites were counted and 40-mite samples from each board were plated as described above in Example 3. Data were analyzed as described above in Example 3.

Conidia density was $1.26 \times 10^{10}$ conidia per gram formulation with a viability of about 91%. Because of large quantities of formulation observed on the sticky boards after treatment, the first sample after treatment was not included in any analysis. One treated hive was found to have either swarmed or died during the course of the Lattes experiment; data for that hive were not included in the analyses. Percentage infection data for one week, November 1-7, was lost due to contamination. A mixed-model analysis of the percentage infection data showed that all the factors, treatment (F2,7=26.31, p=0.0006), date (F5,35=12.06, p<0.0001) and their interaction (F10,35=2.24, p=0.0384), were significant, and a significantly higher percentage of mites from hives treated with conidia were infected compared to either mites from the powder only treatment or mites from the controls on all dates. Analysis of mite fall showed that date (F7,49=6.81, p<0.0001) and the interaction of treatment and date (F14, 49=49.6, p<0.0001) were significant effects, but treatment was not ($F2,7=0.04$, $p<0.961$). Post hoc analysis did not identify any dates when treatment had a significant effect.

EXAMPLE 5

Another experiment was conducted to a) evaluate the impact of an application of the biopesticide formulation on colony health and on *Varroa* mite fall; and b) examine the effects of substituting the wax powder (see Example 3) with wheat flour, in the biopesticide. Cereal flour has been recommended for wet or humid environments (Burges, Formulation of Microbial Biopesticides: Beneficial Microorganisms, Nematodes and Seed Treatments, Kluwer Academic Publishers, Dordrecht, The Netherlands, pages 131-185, 1998). However, flour is comparatively hygroscopic (Rückhold et al., Food Control, Volume 12, pages 401-407,2001) and, unlike plant wax powder, is not inert because it is a source of nutrients for germinating conidia (Burges, 1998, supra). This experiment was conducted at the start of a nectar flow, when brood densities and foraging activity are high and the sensitivity of hives to a perturbation likewise high. Widespread infection within a colony would be expected to measurably affect adult bee and brood populations, and possibly colony food stores and weight gain. Cultures of *B. bassiana* isolate Bb05002 were prepared as in Example 3. Three formulations were prepared with the *B. bassiana* conidia: carnauba wax powder and conidia ("powder+conidia"); wheat flour and conidia ("flour+conidia"); and wheat flour alone ("flour alone"). Each dose of powder+conidia consisted of 1.0 g Bb05002 conidia mixed with 9.0 g ENTOSTAT® powder and 0.05 g hydrated silica (Hi-Sil-233) as in Example 3. Each dose of flour+conidia consisted of 1.0 g Bb05002 conidia mixed with 9.0 g commercially-prepared wheat flour (type 55, Générale des Farines France, Paris, France) and 0.05 g Hi-Sil-233. Each dose of flour alone was 10.0 g wheat flour mixed with 0.05 g Hi-Sil-233. Cfu density at time of treatment was 1.96×1010 cfu/g for the powder+conidia formulation, and 6.33×109 cfu/g for the flour+conidia formulation. Five colonies were treated with powder+conidia, 5 colonies with flour+conidia, 4 colonies with flour alone, with 7 colonies kept as untreated controls. Treatments were randomly assigned, but at least one untreated colony was placed between all treated colonies. Formulation was applied as in Example 3. The daily mite fall and infection rate of the fallen mites were determined as in Example 3. Mite fall and infection was measured starting 2 weeks before application and continuing for about a month after application. The bee colonies were kept in the same type of hives as in Example 3.

As a measure of colony health, each hive was weighed every week, starting a week before application, using a portable electronic balance, and these data were used to calculate the daily colony growth rate. Just before biopesticide application, all hive parts (brood box, lid, base and frames) were shaken free of bees and weighed. Digital photographs were taken of each side of each frame using a 3.3 megapixel camera (Nikon Coolpix 990, Tokyo, Japan), and the area of capped brood and honey per photograph was estimated using ArcView 3.0 (Environmental Systems Research Institute, Redlands, Calif., USA). Brood areas were inspected closely for any signs of fungal infection. The hive was then reassembled, the bees replaced and a "super" (a second box placed on top of the main hive body and where the bees store most of their honey) with frames was weighed and placed on top of each colony. Four weeks after application, all the hive parts were weighed again, the frames photographed and analyzed, and the data used to calculate the adult bee population size and the amounts of bee brood and capped honey. For colony weights, total adult bee weights and capped brood surface area, the growth rate was calculated by dividing the post treatment value by the pretreatment value. In the analysis of the daily growth rate in colony weight, treatment ($F_{3,97}$=7.10, p=0.0002), and date ($F_{4,97}$=25.53, p<0.0001) were significant factors, but their interaction was not (p=0.840) (FIG. 6). The values for powder+conidia ($t_{97}$=2.94, p=0.0041), flour+conidia ($t_{97}$=2.49, p=0.0146), and flour alone ($t_{97}$=4.40, p<0.0001) were all significantly higher than the control, using the Bonferroni adjustment for the t-value probability. Treatment was not significant in the analysis of the daily growth rate for total adult weight (p=0.380), capped brood surface area (p=6.754), or capped honey (p=0.728) (Table 2). No infected brood were observed in any photographs. Thus, treatment of hives with *B. bassiana* had no observable effect on colony health.

In the analysis of the proportion of infected mites, treatment ($F_{3,37}$=15.07, p<0.0001), date ($F_{9,55}$=20.82; p<0.0001) and treatment×date interaction ($F_{27,55}$=4.07, p<0.0001) were all significant (FIG. 7A). The proportions of infected mites in both the powder+conidia ($t_{37}$=4.91, adj. p<0.001) and the flour+conidia ($t_{37}$=5.64, adj. p<0.0001) groups were significantly higher than the control whereas the flour alone group was not (adj. p=0.785). Elevated densities of infected mites, probably due to bee drift or robbing, were also observed. In the analysis of mite fall on to sticky boards, treatment ($F_{3,206}$=7.33, p<0.0001) was significant but neither date (p=0.37) nor interaction (p=0.999) were (FIG. 7B). Compared to the control group mite fall was significantly higher in the powder+conidia group ($t_{227}$=4.33, adj. p<0.0001) and the flour alone group ($t_{227}$=3.07, adj. p=0.0143) but not in the flour+conidia group (adj. p=0.99). Likewise, mite fall in the powder+conidia group was significantly higher than in the flour+conidia group ($t_{227}$=2.80, adj. p=0.0334) but not the flour alone group (p=0.99). The flour+conidia and flour alone groups were not significantly different (adj. p=0.51). Thus mite fall in the powder+conidia treatment was significantly higher than that in control whereas the flour+conidia treatment was not, although those two treatments were themselves not significantly different. Inspection of mite fall data over time does suggest a somewhat different dynamic, even if not born out by statistical significance.

TABLE 2

Total adult weight, and total surface areas of sealed brood and honey, for bee colonies before and after treatment with a formulation of *B. bassiana* conidia.

| | | | 23 May | | 27 June | | |
|---|---|---|---|---|---|---|---|
| Variable | Treatment | N | avg[1] | s.d. | avg[1] | s.d. | Daily r |
| Total adult weight | Powder + conidia | 5 | 3.301 ab | 0.899 | 4.773 a | 0.954 | 0.0105 |
| | Flour + conidia | 5 | 2.805 b | 0.575 | 4.245 ab | 0.535 | 0.0118 |
| | Flour alone | 4 | 4.305 a | 0.513 | 4.711 ab | 0.866 | 0.0026 |
| | Control | 7 | 2.161 b | 0.865 | 3.242 b | 1.083 | 0.0116 |

TABLE 2-continued Total adult weight, and total surface areas of sealed brood and honey, for bee colonies before and after treatment with a formulation of *B. bassiana* conidia.

| Variable | Treatment | N | 23 May avg[1] | s.d. | 27 June avg[1] | s.d. | Daily r |
|---|---|---|---|---|---|---|---|
| Sealed brood surface area | Powder + conidia | 5 | 4532 a | 551 | 3712 a | 732 | −0.0057 |
| | Flour + conidia | 5 | 3721 ab | 982 | 3665 a | 596 | −0.0004 |
| | Flour alone | 4 | 4447 a | 548 | 3790 a | 587 | −0.0046 |
| | Control | 7 | 2867 b | 1105 | 2812 a | 1018 | −0.0006 |
| Sealed honey surface area | Powder + conidia | 5 | 4846 a | 1800 | 5489 a | 1099 | 0.0036 |
| | Flour + conidia | 5 | 2836 a | 1750 | 3593 a | 1870 | 0.0068 |
| | Flour alone | 4 | 4535 a | 849 | 6009 a | 1545 | 0.0080 |
| | Control | 7 | 4516 a | 1431 | 5203 a | 2524 | 0.0040 |

[1]Averages within a variable and within a date followed by different letters are signficantly different using Tukey's HSD at p < 0.05

EXAMPLE 6

In another experiment, similar to Examples 3 and 4, 26 hives were selected for a field experiment. Balances were not used. Sticky boards were placed under all hives starting 3 weeks prior to treatment and replaced at least twice per week thereafter. Formulation was made containing 1.0 gram of strain Bb05002 conidia plus approximately 10 grams of carnauba wax powder (the powder was produced by Strahl & Pitsch Inc., West Babylon, N.Y., USA, and obtained from Rossow Cosmétique, Gennevilliers, France) plus approximately 0.05 grams hydrated silica (HiSil). The density of conidia per gram of formulation was about $3.70 \times 10^{10}$. Five hives were each treated twice, applications one week apart, using the technique described in Example 3. Similarly, formulation was prepared using *B. bassiana* strain GHA (EPA Registration No. 70810-8; an active ingredient in Botanigard®, produced by Emerald BioAgriculture Corp.) to test whether the use of another isolate of *B. bassiana* affects the distribution of the product among the bees or the infection rates of the *Varroa* mites. The number of conidia per gram for that formulation was about $1.72 \times 10^{10}$. Five different hives were treated twice with this formulation. A third formulation was prepared using Bb05002 and candelilla wax powder (also produced by Strahl & Pitsch Inc., NY, and obtained from Rossow Cosmétique, France) to test whether the use of another hard plant wax powder affects spore distribution or mite infection rates; the number of conidia per gram was about $1.76 \times 10^{10}$ and 5 hives were treated once. Five hives were treated twice with the candelilla powder only as a blank control to observe the effects of the powder on the bees and on the *Varroa* mites, and 6 hives were left untreated as controls. Sticky boards were replaced every 3-4 days after treatment for about three weeks and weekly thereafter for about two weeks. All mites were counted and 40-mite samples from each board were plated as described above in Example 3. Samples of live bees were taken as in Example 3. Data were analyzed as described above in Example 3.

Figure 8:
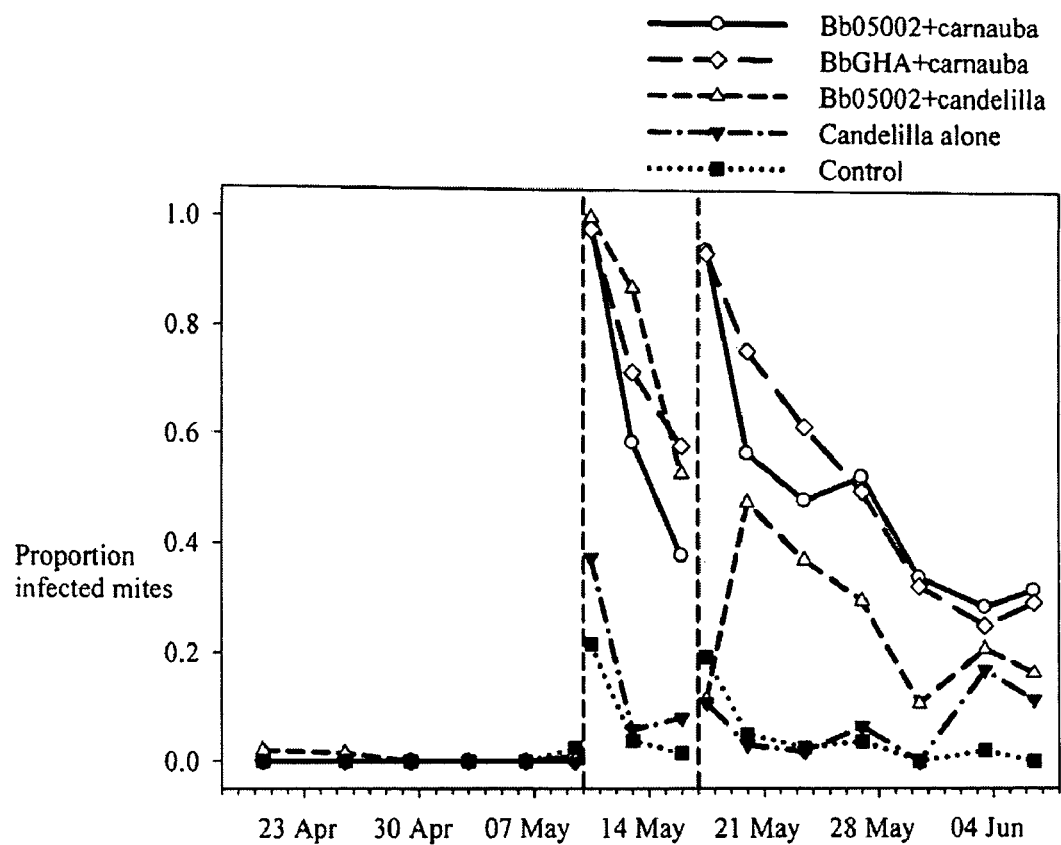

As in examples 3 and 4, the first mite sample after treatment was not included in the analysis of proportion infection. At least one infected mite was found in 3 of the experimental hives during the 3 weeks before application. A mixed-model analysis of the percentage infection data showed that treatment ($F_{4,160}$=62.45, p<0.0001), date ($F_{7,160}$=7.50, p<0.0001) and the treatment×date interaction ($F_{28,160}$=1.77, p=0.0150) were all significant factors (FIG. 8). In post hoc contrasts treatment was a significant factor (p always <0.0001) for all dates up to 12 days after the last application. Treatment was not significant for mites collected 16 days after the last treatment, but it was again significant (p=0.0027) for mites collected on 19 days after the last treatment. The proportion of infected mites in the treatments Bb05002+carnauba, BbGHA+carnauba, and Bb05002+candelilla were significantly different from zero for all days (statistical probability always <0.0001). Among the hives not treated with spores, the only occasion on which the proportion of infected mites rose to significance occurred with the candelilla wax alone treatment for mites collected 16 days after the last treatment. Infected mites were also found in hives not treated with conidia, probably due to bee drift or robbing.

Figure 9:
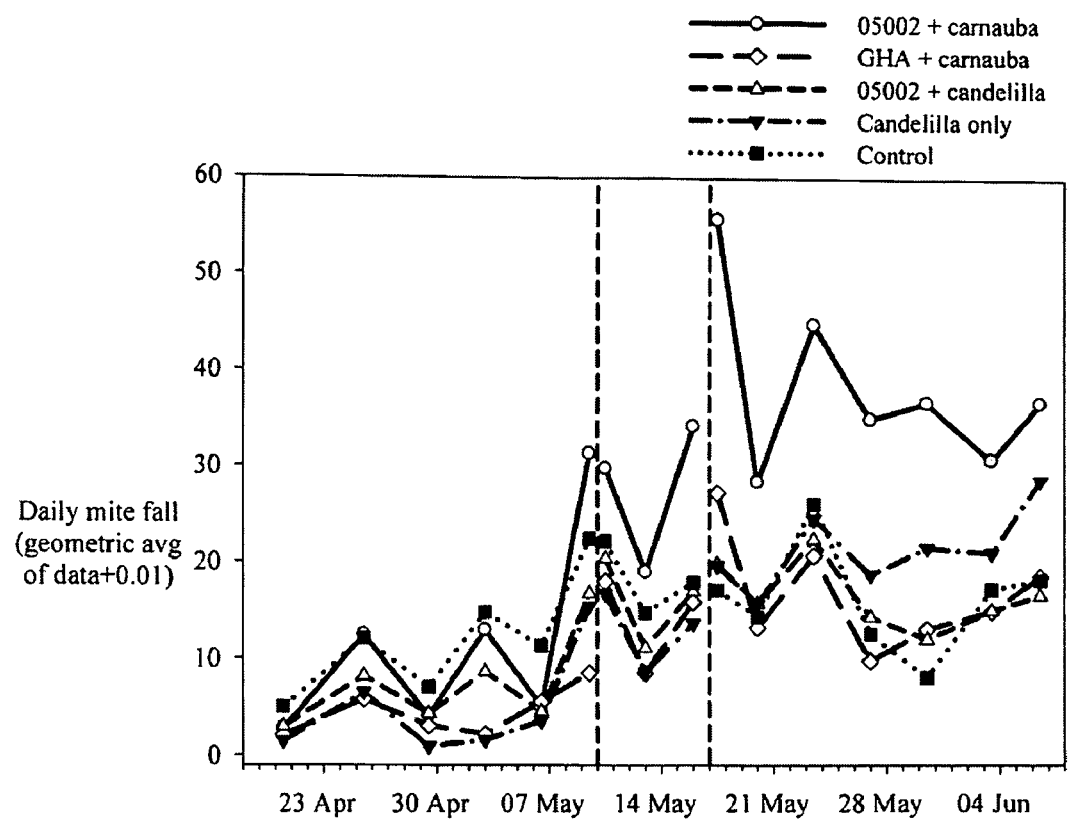

In the analysis of mite fall, treatment was significant ($F_{2,245}$=4.94, p=0.0008) but neither date (p=0.999) nor treatment×date (p=0.999) were (FIG. 9). Post hoc contrasts showed that mite fall in hives treated with 05002+carnauba was significantly higher than in hives treated with candelilla powder alone ($t_{245}$=4.35, p=0.0002).

Figure 10:
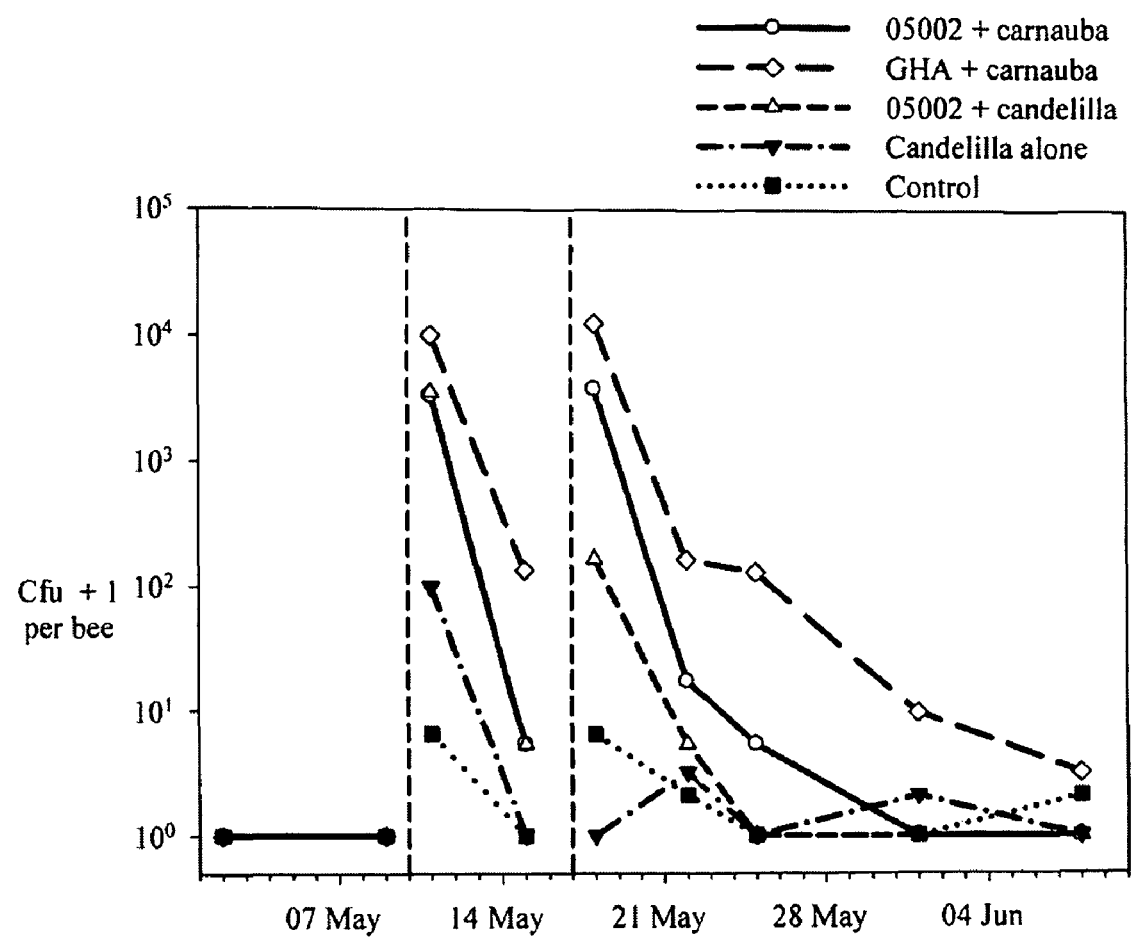

The statistical analysis of cfu density was conducted in the same manner as for the proportion of infected mites above. Before application, no *B. bassiana* cfu were observed in any bee samples. Treatment ($F_{4,70}$=42.99, p<0.0001), date ($F_{6,70}$=43.11, p<0.0001) and treatment×date ($F_{24,70}$=5.59; p<0.0001) were significant factors overall (FIG. 10). After application, treatment was a significant factor on all days until the samples collected 12 days after the second application, after which treatment was no longer a significant factor. The day after the 1st application cfu densities in the Bb05002+carnauba ($t_{70}$=10.54, p<0.0001), BbGHA+carnauba ($t_{70}$=12.81, p<0.0001) and Bb05002+candelilla ($t_{70}$=11.33, p<0.0001) were all significantly different from 0 but in the next sample 4 days later only the cfu density in the BbGHA+carnauba treatment was significant. In the samples collected just after the 2nd application, all 3 treatments using *B. bassiana* were significant but by the next sample 4 days later only the BbGHA+carnauba treatment was significant; it remained so until the last sample. Thus, the formulation was distributed among bees and caused infection in *Varroa* mites whether isolates Bb05002 or GHA were used, or whether carnauba or candelilla wax powder was used.

EXAMPLE 7

In another experiment, similar to Examples 3, 4, 5, and 6, thirty-two hives were selected to evaluate multiple treatments of *B. bassiana* formulation. Sticky boards were placed under all hives two weeks prior to treatment and replaced just after application. Formulation was made containing 0.6 gram of strain Bb05002 conidia plus approximately 9 grams of carnauba wax powder (produced by Strahl & Pitsch Inc., as in Example 4) plus approximately 0.05 grams Hi-Sil-233. Because of the quantity of conidia required, 2 batches of conidia were produced. The density of conidia per gram of formulation was about $1.80 \times 10^{10}$ for the first 2 applications and $3.36 \times 10^9$ for the third application. Nine hives were each treated three times with formulation, applications 10 days apart, using the technique described in Examples 3, 4, and 5. Ten hives were treated three times with carnauba powder and Hi-Sil-233 as a blank control, as in Example 3, and 13 hives were left untreated as controls. Sticky boards were replaced every 3-4 days before and after treatment. All mites were counted.

Figure 11:
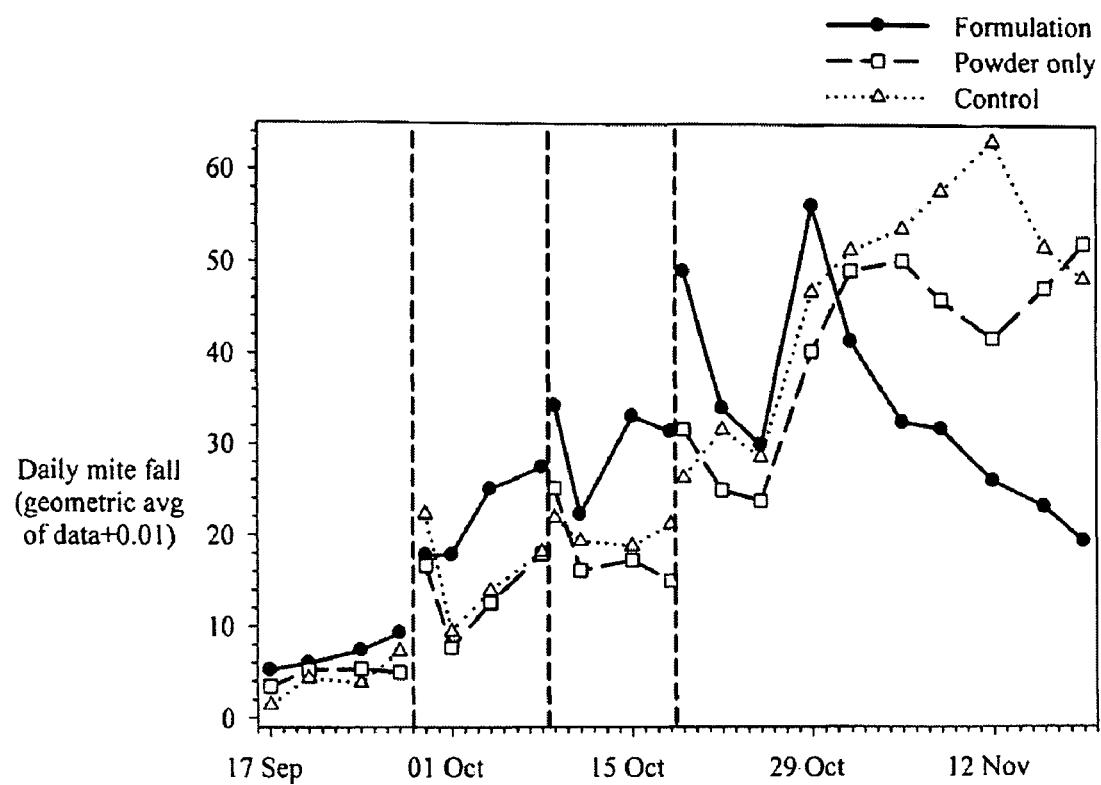
FIG. 11 is a graph showing the average (geometric) daily mite fall on to sticky boards over time for colonies treated with either *B. bassiana* isolate 05002 conidia plus carnauba wax powder (applied 3 times), carnauba wax powder alone (applied 3 times), or nothing (control). Vertical dashed line shows day of treatment.
Figure 12:
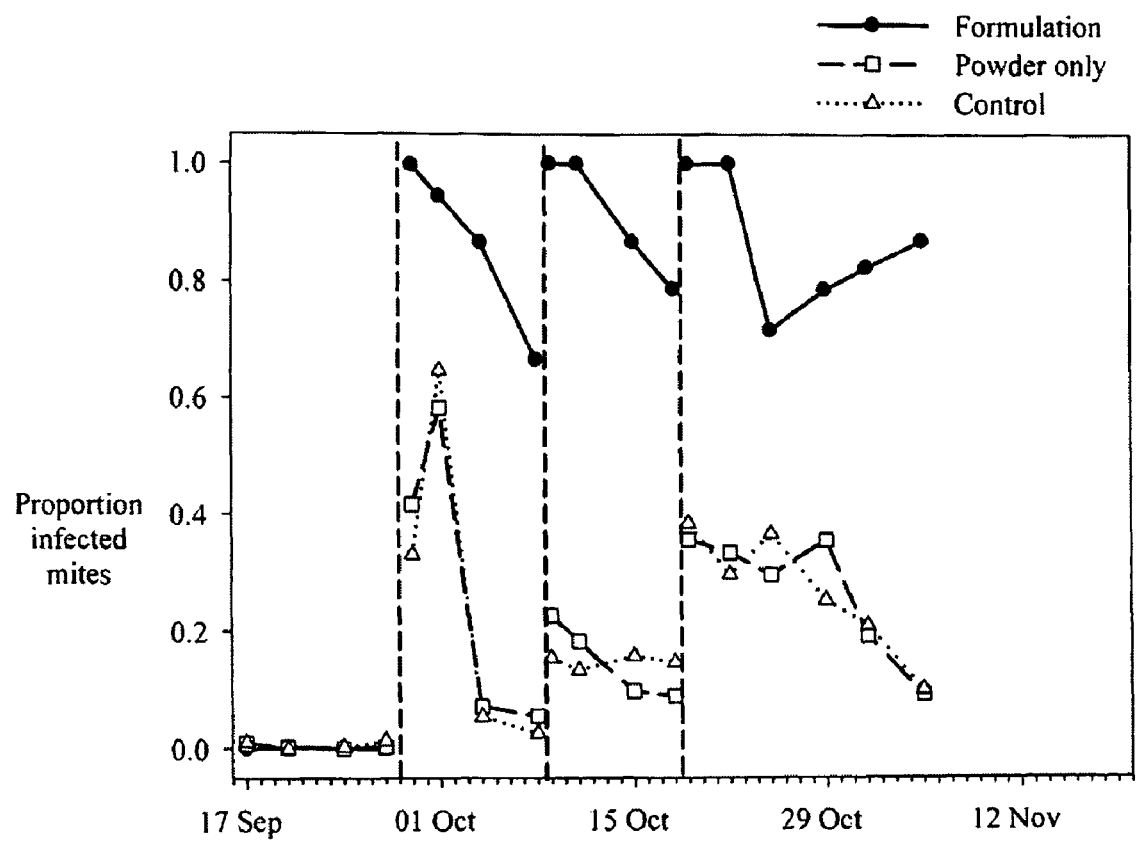
FIG. 12 is a graph showing the average proportion fallen mites that were infected per colony over time for bee colonies treated with either *B. bassiana* isolate 05002 conidia plus carnauba wax powder (applied 3 times), carnauba wax powder alone (applied 3 times), or nothing (control). Vertical dashed line shows day of treatment.

Mite fall was evaluated using a mixed-model analysis of covariance, using the average mite fall before treatment as a covariate. Treatment ($F_{2,497}$=8.81, p=0.0002), date ($F_{17,497}$=13.05, p<0.0001) and treatment×date ($F_{34,497}$=2.08, p=0.0005) were all significant, as was the covariate ($F_{1,497}$=842.16, p<0.0001) (FIG. 11). In post hoc contrasts, mite fall in hives treated with conidia was significantly lower than that of control hives ($t_{497}$=4.12, p=0.0001). Hives treated with powder only were not significantly different from control hives (p=0.052) or from hives treated with conidia (p=0.322). The proportion of the fallen mites showing infection was analyzed using a simple repeated-measure MANOVA, and showed that hives treated with formulated conidia were indeed significantly higher than either control hives ($F_{1,29}$=226.07, p<0.0001) or hives treated with powder only ($F_{1,29}$=194,34, p<0.0001) (FIG. 12). Thus, in this experiment, mite fall relative to pre-treatment was significantly lower in treated hives than in control hives, and significant numbers of infected mites were observed for each sampling after the first treatment until at least 17 days after the third treatment.

The foregoing detailed description is for the purpose of illustration. Such detail is solely for that purpose and those skilled in the art can make variations without departing from the spirit and scope of the invention.

We claim:

1. A biologically pure culture of *Beauvaria bassiana* strain NRRL 30976.

2. A biopesticidal composition comprising a biopesticidal effective amount of a biologically pure culture of *Beauvaria bassiana* strain NRRL 30976 and an agriculturally acceptable carrier.

3. The composition of claim 2 wherein the *Beauvaria bassiana* strain is in the form of spores.

4. The composition of claim 2 wherein the agriculturally acceptable carrier is a plant hard wax powder.

5. The composition of claim 4 wherein said plant hard wax powder is selected from the group consisting of carnuba wax powder, candelilla wax powder, jojoba wax powder, and mixtures thereof.

* * * * *